(12) United States Patent
Huang et al.

(10) Patent No.: US 7,645,915 B2
(45) Date of Patent: Jan. 12, 2010

(54) COMPOSITE DRESSING

(75) Inventors: Ching-Cheng Huang, Wugu Township, Taipei County (TW); Su-Huei Lai, Wugu Township, Taipei County (TW); Yung-Sheng Lin, Sioushuei Township, Changhua County (TW); Ting-Kai Leung, Taipei (TW)

(73) Assignees: Medical and Pharmaceutical Industry Technology and Development Center, Taipei County (TW); National Applied Research Laboratories, Taipei (TW)

( * ) Notice: Subject to any disclaimer, the term of this patent is extended or adjusted under 35 U.S.C. 154(b) by 12 days.

(21) Appl. No.: 12/001,291

(22) Filed: Dec. 11, 2007

(65) Prior Publication Data

US 2009/0043235 A1 Feb. 12, 2009

(30) Foreign Application Priority Data

Aug. 8, 2007 (TW) .............................. 96129301 A

(51) Int. Cl.
*A61F 13/00* (2006.01)

(52) U.S. Cl. .......................................... 602/42; 602/48

(58) Field of Classification Search .............. 602/41–59
See application file for complete search history.

(56) References Cited

U.S. PATENT DOCUMENTS

| 6,333,093 | B1 * | 12/2001 | Burrell et al. | ............... | 428/194 |
| 6,797,396 | B1 * | 9/2004 | Liu et al. | ..................... | 428/483 |
| 7,137,968 | B1 * | 11/2006 | Burrell et al. | ............... | 604/180 |
| 7,291,762 | B2 * | 11/2007 | Flick | ........................... | 602/48 |

FOREIGN PATENT DOCUMENTS

| TW | 590763 | 6/2004 |
| TW | 1247614 | 2/2006 |

* cited by examiner

*Primary Examiner*—Michael A. Brown
(74) *Attorney, Agent, or Firm*—Porzio, Bromberg & Newman, P.C.

(57) ABSTRACT

A composite dressing including a first polymeric layer, a second polymeric layer, a metal oxide, and a pharmaceutical active material is provided. The second polymeric layer is biocompatible and is disposed on a surface of the first polymeric layer. The metal oxide is distributed inside or on at least one surface of the first polymeric layer, while the pharmaceutical active material is distributed inside or on at least one surface of the second polymeric layer.

20 Claims, 2 Drawing Sheets

COMPOSITE DRESSING

FIELD OF THE INVENTION

The present invention relates to a composite dressing, and more particularly to a composite dressing containing the metal oxide for the medical use.

BACKGROUND OF THE INVENTION

Currently most medical dressings in the market are porous, waterproof, and moisture-permeable for the comfort and convenience in the usage. A lot of newly developed biomedical materials with such properties have been applied in the market of the medical dressings. The biomedical materials come from nature or synthetic materials. The biomedical materials are biocompatible, and can be implanted into living biological system in order to replace or to mend a part of the living biological system, or directly contact with the living biological system to implement its life function. For example, the Taiwan Patent No. I247614 has disclosed a medical dressing with the reinforcing function, where the medical dressing uses biocompatible material to afford the space for the growth of the regenerated cells.

Besides that the requirements for the material of the medical dressing become stricter, several medical dressings further have the antiseptic function to prevent the invasion of the bacteria. Both the above-mentioned Taiwan Patent No. I247614 and the Publication No. 00590763 disclose the medical dressings with the functions of antiseptics and promoting the growth rate of the cell regeneration by doping the nanoparticles of gold or silver into the medical dressings.

After a lot of trials and improvements, the inventors develop a "composite dressing", which replaces the nanoparticles of gold or silver by metal oxide. Not only is the cost of the invented product lower, but also the invented product has all the advantages of the current technologies. Furthermore the invented product can improve the effective absorption of the drug by the human body, and this function is not available for the current products. The present invention is described below.

SUMMARY OF THE INVENTION

In accordance with one aspect of the present invention, a composite dressing containing metal oxide is provided. The cost of this composite dressing is lower than those of the current products, and the addition of the metal oxide can perform several functions, which are not available for the current products. These functions includes, for example, better absorption of the drug by the human body, accelerating the blood circulation, activating metabolism, promoting the ability of biological tissue regeneration, activating immune system, etc.

In accordance with one aspect of the present invention, a composite dressing including a first polymeric layer, a second polymeric layer, and metal oxide is provided. The second polymeric layer is disposed on at least one surface of the first polymeric layer. The metal oxide is distributed in one selected from a group consisting of in the first polymeric layer, on the at least one surface of the first polymeric layer and a combination of the both.

Preferably, the composite dressing further includes a pharmaceutical active material distributed in one selected from a group consisting of in the second polymeric layer, on at least one air contacting surface of the second polymeric layer and a combination of the both.

Preferably, the pharmaceutical active material is a non-steroid anti-inflammatory drug.

Preferably, the first polymeric layer is made by a cross-linking reaction and has a cross-linked structure.

Preferably, the first polymeric layer is made of a cross-linkable polymer containing an amine group.

Preferably, the first polymeric layer is made of at least one selected from a group consisting of polyurethane, polyester, polyethylene, polyimide, polyamide, polyamide-imide, chitosan, polysaccharide, polyvinylpyrrolidone, cellulose, polylactic acid, and polyether.

Preferably, the second polymeric layer is made by a cross-linking reaction and has a cross-linked structure.

Preferably, the second polymeric layer is biocompatible.

Preferably, the second polymeric layer is made of at least one selected from a group consisting of chitosan, sodium alginate, polysaccharide, polyvinylpyrrolidone, poly-2-hydroxyethyl methacrylate, polyvinyl alcohol, cellulose, hyaluronic acid, collagen, and polylactic acid.

Preferably, the second polymeric layer is made of hydrogel.

Preferably, the first and the second polymeric layers are made of different materials.

Preferably, the first and the second polymeric layers are made of the same material.

Preferably, the first and the second polymeric layers are waterproof and moisture-permeable.

Preferably, the first and the second polymeric layers have elasticity and extensibility.

Preferably, the second polymeric layer is distributed on at least one surface of the first polymeric layer by a coating method.

Preferably, the second polymeric layer is distributed on at least one surface of the first polymeric layer by a dipping method.

Preferably, the metal oxide comprises one selected from a group consisting of aluminum oxide, magnesium oxide, and iron oxide.

Preferably, the composite dressing is a composite medical dressing.

Preferably, the metal oxide has a weight percentage of 0.1% to 40% relative to a total weight of the first polymeric layer and the metal oxide.

In accordance with another aspect of the present invention, a composite dressing including a first polymeric layer, a second polymeric layer, and a metal oxide is provided. The second polymeric layer strengthens the first polymeric layer. The metal oxide is distributed in one selected from a group consisting of in the first polymeric layer, on the at least one surface of the first polymeric layer and a combination of the both.

Preferably, the second polymeric layer is disposed in one of inside the first polymeric layer and on a surface of the first polymeric layer.

The above objects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

Figure 1:
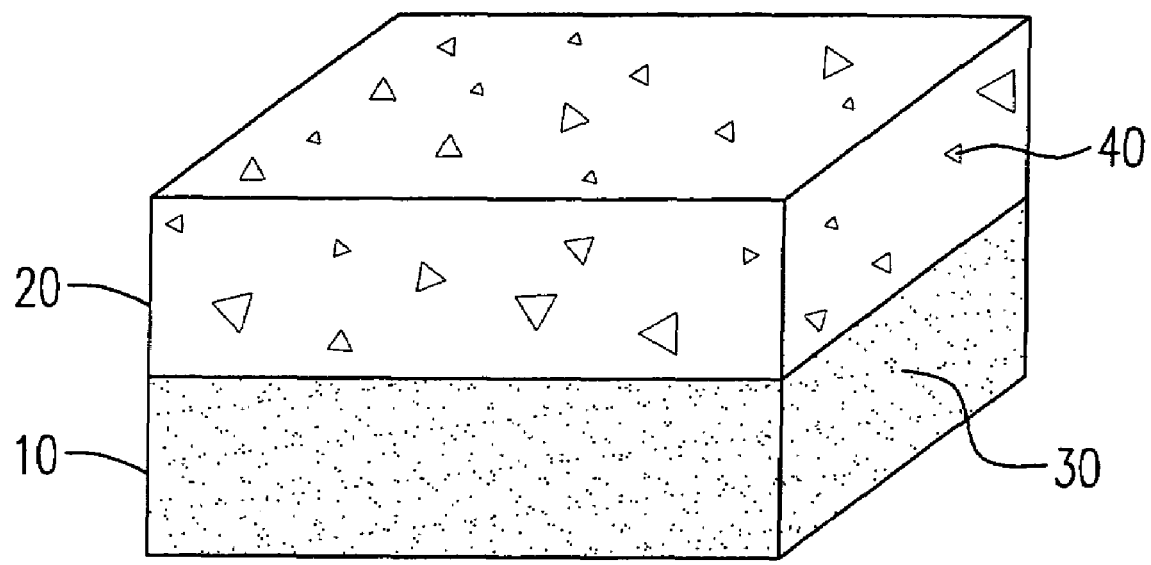
FIG. 1 is a schematic diagram showing the composite dressing according to a preferred embodiment of the present invention.

Please refer to FIG. 1, which is a schematic diagram showing the composite dressing according to a preferred embodiment of the present invention. As shown in FIG. 1, the composite dressing 1 includes a first polymeric layer 10, a second polymeric layer 20 disposed on the first polymeric layer 10, metal oxide 30 distributed in the first polymeric layer 10, and a pharmaceutical active material 40 distributed in the second polymeric layer 20. The metal oxide 30 can be disposed on a surface of the first polymeric layer 10. However the metal oxide 30 is a strong base. Thus, when the metal oxide 30 is disposed on a surface of the first polymeric layer 10, it is better to cover the metal oxide 30 with the second polymeric layer 20 to avoid the direct contact between the human skin and metal oxide 30. The pharmaceutical active material 40 can be disposed on the air contacting surface of the second polymeric layer 20. Depending on the practical requirements, the pharmaceutical active material 40 can be antibiotics, anti-inflammatory, or the drug for promoting the regeneration of the skin tissue, etc. One of the major purposes of the first polymeric layer 10 is to provide the strength support for the second polymeric layer 20, so the material of the first polymeric layer 10 can be chosen from the polymers able to afford the strength support. On the other hand, since the second polymeric layer 20 is directly contacted with the skin, the biocompatibility can be an important characteristic for the second polymeric layer 20. The first and the second polymeric layers 10, 20 can be made of the same or different materials.

Figure 2:
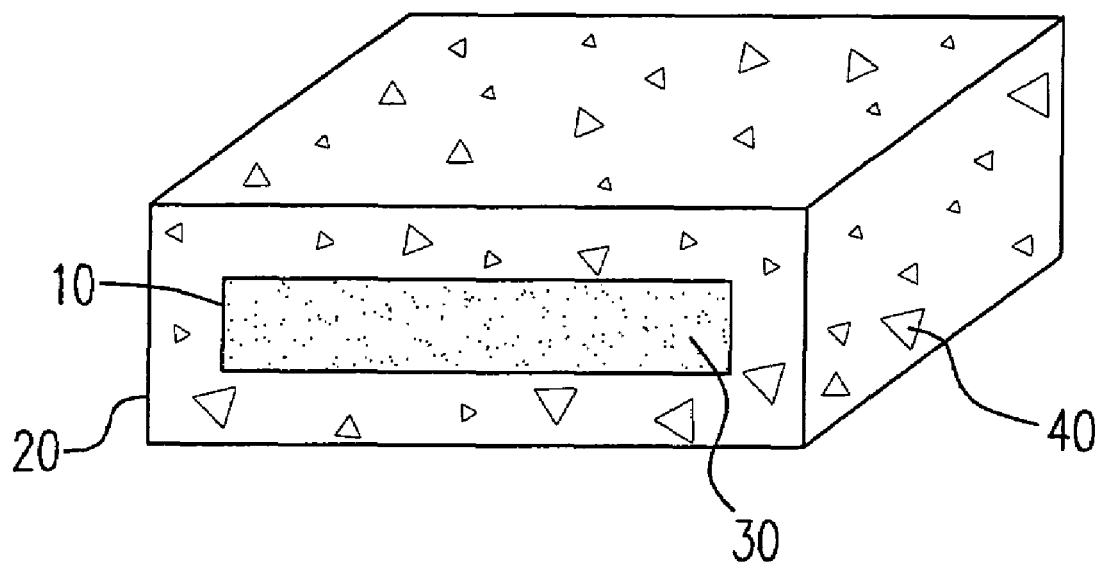
FIG. 2 is a schematic diagram showing the composite dressing according to another preferred embodiment of the present invention.

Please refer to FIG. 2, which is a schematic diagram showing the composite dressing according to another preferred embodiment of the present invention. As shown in FIG. 2, the composite dressing 2 includes a first polymeric layer 10, a second polymeric layer 20 covering the first polymeric layer 10, metal oxide 30 distributed in the first polymeric layer 10, and pharmaceutical active material 40 distributed in the second polymeric layer 20. After the first polymeric layer 10 is made, it can be dipped into the solution containing the material of the second polymeric layer 20 by the dipping method, so the second polymeric layer 20 can uniformly and completely cover the first polymeric layer 10 to obtain the composite dressing 2. To produce the composite dressing 1 by the dipping method can be done by the following processes. First, the cross-linking agent is applied to a surface of the first polymeric layer 10, which is then dipped into the solution containing the material of the second polymeric layer 20. The second polymer is reacted with the cross-linking agent, so the second polymeric layer 20 can be formed on a surface of the first polymeric layer 10.

Please refer to FIGS. 1 and 2, the metal oxides 30 in the composite dressings 1 and 2 come from the natural minerals, including at least one of aluminum oxide, magnesium oxide, and iron oxide. Other constituents include titanium oxide, titanium boride, silicon oxide, zinc hydroxide, zinc oxide, or carbide. One preferred metal oxide 30 contains at least one of 60-95% aluminum oxide, 1-20% iron oxide and 1-10% magnesium oxide. The metal oxide of this invention has antiseptic effect to *Staphylococcus aureus* and *Escherichia coli* higher than 99.9%, according to the AATCC 100 testing standards of USA. In addition, the negative ions are detected, but no ionizing radiation is detected in the measurements. The ionizing radiation is considered to be dangerous for invoking the genetic mutation and generating the cancer. The product of this invention is quite safe for health, though it directly contacts with the human skin.

The metal oxide 30 in this invention can promote the absorption of pharmaceutical active material 40 by the human body. Besides, the metal oxide 30 can cause the resonance of the water molecules in the human body and turn large water molecular aggregates into small water molecular aggregates in order to raise the oxygen content in the human body. Furthermore, the resonance effect of the water molecules can slightly increase the hypodermic temperature, expand blood vessel, decrease the viscosity and surface tension of the blood, accelerate blood circulation, improve the circulation system of the human body, quicken the heal-over of the wound, relieve the pain of the joint. Therefore, even if the composite dressings 1 and 2 are not added with any pharmaceutical active material 40, the above basic effects still remain.

For better understanding the spirit and technical features of this invention for the skilled person in this field, eight embodiments are provided below for the further explanation of specific content of this invention.

First Embodiment

Preparation of the Polyurethane Film Dressing Substrate

The amine-containing polymer solution and multi-isocyanate-containing (—N=C=O, isocyanate group) polymer solution are prepared. The amine-containing polymer solution is poured into an iron plate. The minimum required quantity of this solution is the quantity to cover at least a whole top surface of the iron plate. The thickness of the final film can be proportionally controlled by the height of the solution in the iron plate. Then the multi-isocyanate-containing polymer solution as a cross-linking agent solution is added into the amine-containing polymer solution in the iron plate to cause the cross-linking reaction and to form the polyurethane (PU) film.

Another way to form the polyurethane film is to do the coating of the amine-containing polymer solution by the coating machine, then to spay the diluted cross-linking agent on the coating layer, and to keep the temperature at 35° C. for four hours.

In this embodiment, the amine-containing polymer can be replaced by the hydroxy-group-containing polymer.

Second Embodiment

Preparation of the Polyurethane Film Dressing Substrate Containing the Metal Oxide The amine-containing polymer solution and multi-isocyanate-containing polymer solution are prepared. The metal oxide according to a specific ratio can be serially added in several small batches into the amine-containing polymer solution. Then the polyurethane film containing metal oxide can be produced by using the same method as in the first embodiment.

Also the metal oxide according to a specific ratio can be serially added in several small batches into the multi-isocyanate-containing polymer solution as a cross-linking agent solution. Then the polyurethane film containing metal oxide can be produced by using the same method described in the first embodiment.

Third Embodiment

Preparation of the Polyurethane Film Dressing Substrate Containing the Metal Oxide The same method described in the first embodiment is used to produce the polyurethane film. Then the general thin layer forming methods, such as coating, printing, or laminating, can be applied to affix the metal oxide on the surface of the polyurethane film.

Fourth Embodiment

Preparation of the Polyurethane Film Dressing Substrate Containing the Metal Oxide The polyurethane film containing the metal oxide can be produced by using the same method as in the second or the third embodiment. Then the outer surface of this polyurethane film can be coated with a polyurethane solution, or this polyurethane film can be dipped into a polyurethane solution to form another polyurethane layer on the outer surface of this polyurethane film in order to obtain a polyurethane film composite dressing substrate containing the metal oxide.

Fifth Embodiment

Preparation of the Hydrogel Containing Indomethacin

The copolymer of the acrylic acid, such as Carbopol 981, is dispersed in water by high-speed stirring with a stirrer for about 15 minutes to form a homogeneously mixed Carbopol 981 solution. The poly (sodium acrylate) is evenly dispersed in the glycerol to prepare a poly (sodium acrylate) solution. The deionized water, citric acid, and aluminum chloride are mixed by stirring into a homogeneous solution, into which then the poly (sodium acrylate) solution is added to form an evenly mixed solution. After that, this evenly mixed solution is added into the homogeneously mixed Carbopol 981 solution to form a hydrogel, after the appropriate viscosity of this blended solution is reached. Since the non-steroid anti-inflammatory drug, Indomethacin (IDM), does not dissolve in the water, the IDM, surfactant Span-60, and alcohol are evenly mixed according to the weight ratio of 1:4:10, and then are put into the water bath under heating at the temperature range of 60 to 80° C. to dissolve IDM and to form a yellowish IDM solution. The above-mentioned hydrogel and IDM solution according to the weight ration of 10:1 are blended to form an IDM-containing hydrogel.

Sixth Embodiment

Preparation of the Composite Dressing with the Indomethacin-Containing Hydrogel Layer on its Surface The IDM-containing hydrogel is produced by the same method described in the fifth embodiment, while the polyurethane film containing the metal oxide is produced by the same method described in the second or the third embodiment. Then the IDM-containing hydrogel is applied to the polyurethane film containing the metal oxide to form the polyurethane film dressing with the IDM-containing hydrogel layer on its surface.

Seventh Embodiment

Preparation of the Composite Dressing with the Indomethacin-Containing Chitosan Layer on its Surface The chitosan with the deacetylation ratio higher than 85% in an appropriate amount is dissolved in the 2 to 5% acetic acid solution to prepare 2% (weight percentage) chitosan solution. The IDM solution is prepared by the same method described in the fifth embodiment, while the polyurethane film containing the metal oxide is prepared by the same method described in the second or the third embodiment. The IDM solution and the chitosan solution in various weight ratios are evenly mixed, then applied to the surface of the polyurethane film containing the metal oxide, and dried to form the composite dressing with the Indomethacin-containing chitosan layer on its surface.

In this embodiment, the chitosan can be replaced by other biodegradable or biocompatible material, while the polyurethane can be replaced by other general polymers.

Eighth Embodiment

Preparation of the Composite Dressing with the Indomethacin-Containing Sodium Alginate Layer on its Surface The 1 to 2% (weight percentage) sodium alginate solution is prepared by dissolving the sodium alginate in an appropriate amount into the highly pure water. The IDM solution is prepared by the same method as in the fifth embodiment, while the polyurethane film containing the metal oxide is prepared by the same method described in the second or the third embodiment. The IDM solution and the sodium alginate solution in various weight ratios are evenly mixed, then applied to the surface of the polyurethane film containing the metal oxide, and dried to form the metal-oxide-containing polyurethane film dressing with the Indomethacin-containing sodium alginate layer on its surface

Ninth Embodiment

The surface of the composite dressing produced by the method described in one of the first to the eighth embodiments is coated by an adhesive, e.g. acrylics, epoxy, or hot melt adhesive.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:
1. A composite dressing comprising:
a first polymeric layer;
a second polymeric layer disposed on at least one surface of the first polymeric layer; and a metal oxide including a magnesium oxide and an iron oxide, and distributed in the first polymeric layer.

2. The composite dressing as claimed in claim 1 further comprising a pharmaceutical active material distributed in one selected from a group consisting of in the second polymeric layer, on at least one air contacting surface of the second polymeric layer and a combination thereof.

3. The composite dressing as claimed in claim 2 wherein the pharmaceutical active material is a non-steroid anti-inflammatory drug.

4. The composite dressing as claimed in claim 1 wherein the first polymeric layer is made by a cross-linking reaction and has a cross-linked structure.

5. The composite dressing as claimed in claim 1 wherein the first polymeric layer is made of a cross-linkable polymer containing an amine group.

6. The composite dressing as claimed in claim 1 wherein the first polymeric layer is made of at least one selected from a group consisting of polyurethane, polyester, polyethylene, polyimide, polyamide, polyamide-imide, chitosan, polysaccharide, polyvinylpyrrolidone, cellulose, polylactic acid, and polyether.

7. The composite dressing as claimed in claim 1 wherein the second polymeric layer is made by a cross-linking reaction and has a cross-linked structure.

8. The composite dressing as claimed in claim 1 wherein the second polymeric layer is bio compatible.

9. The composite dressing as claimed in claim 8 wherein the second polymeric layer is made of at least one selected from a group consisting of chitosan, sodium alginate, polysaccharide, polyvinylpyrrolidone, poly-2-hydroxyethyl methacrylate, polyvinyl alcohol, cellulose, hyaluronic acid, collagen, and polylactic acid.

10. The composite dressing as claimed in claim 1 wherein the second polymeric layer is made of a hydrogel.

11. The composite dressing as claimed in claim 1 wherein the first and the second polymeric layers are made of different materials.

12. The composite dressing as claimed in claim 1 wherein the first and the second polymeric layers are made of the same material.

13. The composite dressing as claimed in claim 1 wherein the first and the second polymeric layers are waterproof and moisture-permeable.

14. The composite dressing as claimed in claim 1 wherein the first and the second polymeric layers have elasticity and extensibility.

15. The composite dressing as claimed in claim 1 wherein the second polymeric layer is distributed on at least one surface of the first polymeric layer by a coating method.

16. The composite dressing as claimed in claim 1 wherein the second polymeric layer is distributed on at least one surface of the first polymeric layer by a dipping method.

17. The composite dressing as claimed in claim 1 wherein the metal oxide has a weight percentage of 0.1% to 40% relative to a total weight of the first polymeric layer and the metal oxide.

18. A composite dressing comprising:
a first polymeric layer;
a second polymeric layer strengthening the first polymeric layer, and encapsulating the first polymeric layer; and
a metal oxide distributed in one selected from a group consisting of in the first polymeric layer, on the at least one surface of the first polymeric layer and a combination thereof.

19. A composite dressing comprising:
a first polymeric layer;
a second polymeric layer disposed on at least one surface of the first polymeric layer;
a pharmaceutical active material being a non-steroid anti-inflammatory drug, and distributed in a manner selected from a group consisting of in the second polymeric layer, on at least one air contacting surface of the second polymeric layer and a combination thereof; and
a metal oxide distributed in one way selected from a group consisting of in the first polymeric layer, on the at least one surface of the first polymeric layer and a combination thereof.

20. The composite as claimed in claim 19, wherein the non-steroid anti-inflammatory drug includes indomethacin.

* * * * *

UNITED STATES PATENT AND TRADEMARK OFFICE
CERTIFICATE OF CORRECTION

PATENT NO. : 7,645,915 B2 Page 1 of 1
APPLICATION NO. : 12/001291
DATED : January 12, 2010
INVENTOR(S) : Ching-Cheng Huang et al.

It is certified that error appears in the above-identified patent and that said Letters Patent is hereby corrected as shown below:

Title page, please insert the following Assignee to the Assignee information:

--(73)  Assignee: Taipei Medical University, Taipei City (TW)--

Signed and Sealed this

Thirteenth Day of July, 2010

David J. Kappos
*Director of the United States Patent and Trademark Office*